United States Patent [19]

Wavrin

[11] Patent Number: 5,330,353
[45] Date of Patent: Jul. 19, 1994

[54] MATRIX BAND

[76] Inventor: Dennis L. Wavrin, 207 S. Main, Lesueur, Minn. 56058

[21] Appl. No.: 32,630

[22] Filed: Mar. 17, 1993

[51] Int. Cl.$^5$ ............................................. A61C 5/04
[52] U.S. Cl. ...................................... 433/39; 433/226
[58] Field of Search ................... 433/39, 40, 155, 226

[56] References Cited

U.S. PATENT DOCUMENTS

| | | | |
|---|---|---|---|
| 2,466,830 | 4/1949 | Tofflemire | 153/2 |
| 2,594,367 | 4/1952 | Tofflemire | 32/63 |
| 3,421,222 | 1/1969 | Newman | 32/15 |
| 4,500,288 | 2/1985 | von Weissenfluh | 433/40 |
| 4,523,909 | 6/1985 | Lazarus | 433/39 |
| 4,781,583 | 11/1988 | Lazarus | 433/39 |
| 4,824,365 | 4/1989 | von Weissenfluh | 433/40 |

Primary Examiner—Cary E. O'Connor
Attorney, Agent, or Firm—Merchant, Gould, Smith, Edell, Welter & Schmidt

[57] ABSTRACT

A modified metal matrix band includes a plastic member and a metal member. The matrix band 10 includes a first plastic member 12 operatively connected to a metal member 11. In another embodiment, the matrix band 20 includes a plastic member 23 operatively connected at one end to a first metal member 21 and at its other end to a second metal member 22. The metal members are for inserting between contact points of adjacent teeth, while the plastic member is adjacent the prepared cavity area to be filled.

6 Claims, 1 Drawing Sheet

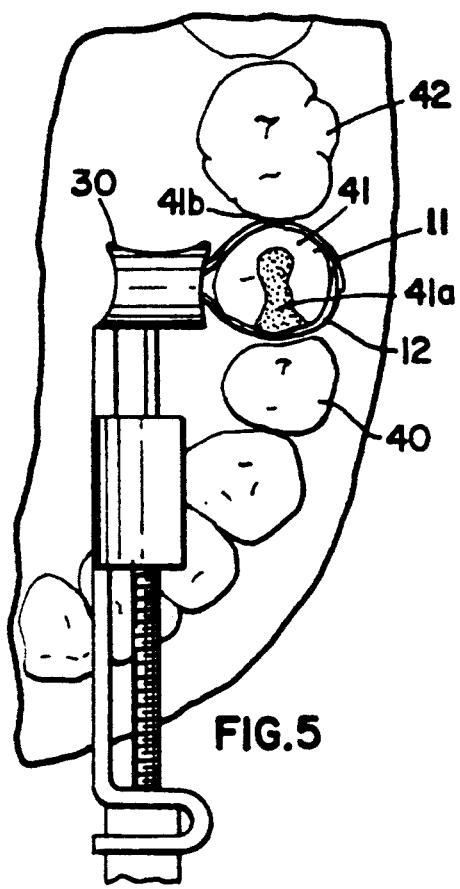
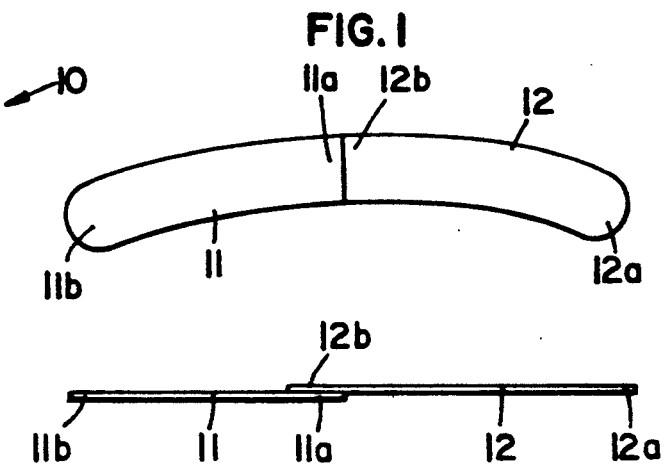
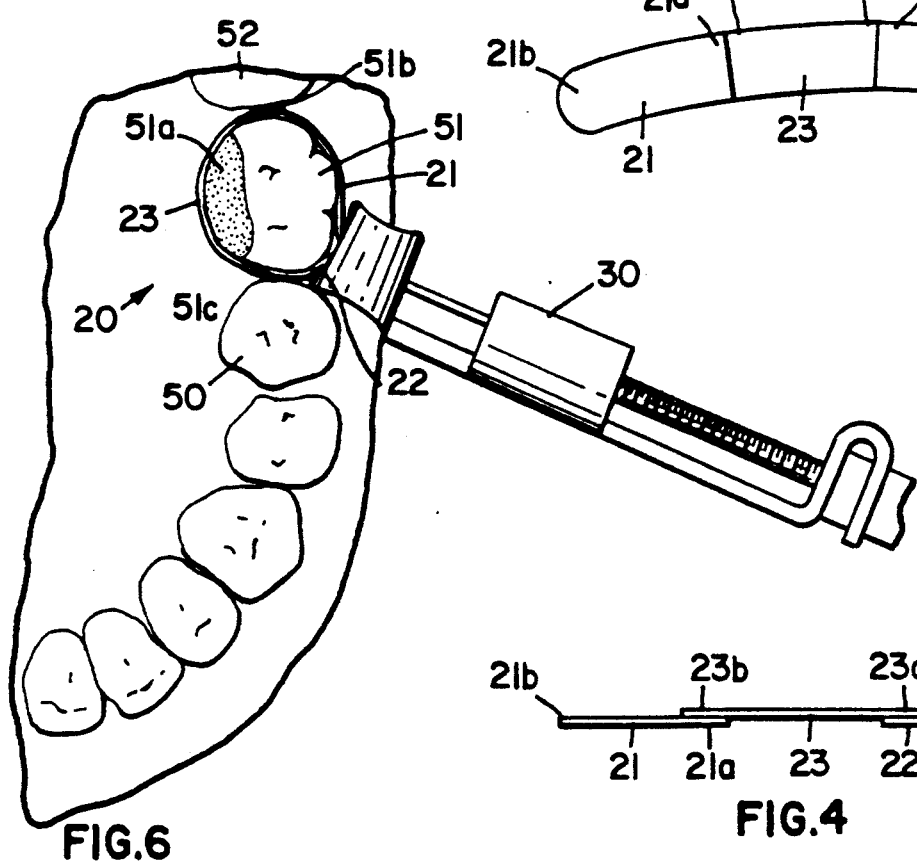

5,330,353

MATRIX BAND

BACKGROUND OF THE INVENTION

1. Field of the Invention

The present invention relates to a dental matrix band, and more particularly to a matrix band having both a metal member and a plastic member.

2. Description of the Prior Art

Matrix bands are well known in the art and, to date, have either been made of all metal or all plastic. The metal matrix bands have typically been used almost exclusively until the development of light-cured posterior composite resins (plastic) fillings for bicuspid and molars that are cured by use of a fiber optic light source.

The formula for these light cured posterior composites was actively developed in the mid-1980's and continue to be modified today. These new posterior composites are specially formulated to resist wear from chewing. Previously developed composite resins (light cured or self cured) were not wear resistant enough to be placed in the back teeth (bicuspids and Molars) where fillings have to endure much more chewing pressure. Light cured posterior composites were developed as a replacement for silver amalgam fillings. They are more aesthetic than silver amalgam because they come in tooth matching colors. There has been some concern in dentistry about the mercury in silver amalgam fillings. The posterior composites contain no mercury.

For these reasons, there has been an increasing interest and use of composite resins in dentistry since the mid-1980's. Dentists want to see any new filling material have a "track record" before they fully accept and use the material. Recently published studies are concluding that these light cured posterior composites do stand up to the increased wear generated in the back teeth. Placing these types of fillings in teeth require difference procedures and skills than are required to place silver amalgam. Patients are showing more and more interest in these fillings primarily because of aesthetic considerations. There have been several instruments and devices that have come on the market in the last year that make placement of light cured posterior composites easier.

A plastic matrix band must be used to place this material because fiber optic light is used to cure it and plastic allows the light to reach the material while keeping it is the proper form in the cavity preparation. The problem with the all plastic matrix bands that are available today arises in the procedure of placing these around the tooth before filling the cavity. After the cavity is drilled out, many times only one side of the tooth is drilled away, and the other side of the tooth is intact and in contact with the adjacent tooth. The adjoining areas are called "contacts" or "contact points". The contacts between the teeth are usually very tight. To get proper form and marginal seal, the matrix band must be fitted around the whole tooth to be filled. The all plastic band can be very difficult to place between the tight contact point because the plastic band is very thin and extremely pliable. The band will usually tear or crumple up and will not slide through the contact point between the teeth. To get the plastic matrix band in place it is usually necessary to "wedge" the tooth. This entails pushing a small piece of wood or plastic that looks like a piece of toothpick between the teeth where the contact point is, thereby separating the teeth enough to allow the plastic band to slip between the contact point. Even with wedging, it is still sometimes difficult if not impossible to get all the plastic band in place. Pushing the wedge between the teeth is not comfortable for the patient and it takes valuable time to allow the teeth to separate. With the use of the wedge there is generally some bleeding of the gums which can contaminate the field of operation. Metal matrix bands are much easier to place between contacts because of their stiffness and very rarely require wedging.

The present invention addresses the problems associated with the prior art matrix bands and allows dentists to place light cured posterior composition resins more easily by giving them a more user friendly matrix band.

SUMMARY OF THE INVENTION

The invention is a modified dental matrix band for engaging around a first tooth having a prepared cavity area and the first tooth having a contact point with a second tooth. The band includes a first plastic member operatively connected to a second metal member, thereby forming a modified matrix band having a metal member for insertion between the first and second teeth at the contact point and the plastic member positioned adjacent the cavity area, wherein a fiber optic light may pass through the plastic member to the prepared cavity area.

In another embodiment, the invention is a modified dental matrix band for engaging around a first tooth having a prepared cavity area and the first tooth having a first contact point with a second tooth and a second contact point with a third tooth. The band includes a first plastic member having first and second ends operatively connected between a second metal member having first and second ends and a third metal member having first and second ends. A modified matrix band is thereby formed having a first metal member for insertion between the first and second teeth at the first contact point and the plastic member positioned adjacent the prepared cavity area and the second metal member for insertion between the first and third teeth at the second contact point, wherein a fiber optic light may pass through the second member to the prepared cavity area.

The invention also includes a method of filling a cavity in a first tooth which has a contact point with a second tooth. The method includes preparing the cavity area to be filled and positioning a matrix band having a metal member and a plastic member around the first tooth so that the metal member is inserted between the first and second tooth at the contact point and positioning the plastic portion proximate the cavity. Then, a light cured composite resin is applied to the cavity and the composite resin is cured with a light.

The invention also includes a method of filling a cavity in a first tooth, the first tooth having a first contact point with a second tooth and a second contact point with a third tooth. The method includes preparing the cavity to be filled, and positioning a matrix band, having a plastic member positioned between a first metal member and a second metal member, around the first tooth so that the first metal member is inserted between the first and second teeth at the first contact point and the second metal member is inserted between the first and third teeth at the second contact point. The plastic portion is positioned proximate the cavity. Then, a light cured composite resin is applied to the cavity and the composite resin is cured with a light.

BRIEF DESCRIPTION OF THE DRAWINGS

FIG. 1 is a top plan view of a matrix band incorporating the present invention;

FIG. 2 is a side elevational view of the band shown in FIG. 1;

FIG. 3 is a top plan view of a second embodiment of the matrix band incorporating the present invention;

FIG. 4 is a side elevational view of the matrix band shown in FIG. 3;

FIG. 5 is a schematic representation of the matrix band shown in FIG. 1 in use;

FIG. 6 is a schematic representation of the matrix band shown in FIG. 3 is use.

DETAILED DESCRIPTION OF THE PREFERRED EMBODIMENT

Referring to the drawings, wherein like numerals represent like parts throughout the several views, there is generally disclosed at 10 a modified matrix band. The matrix band 10 includes a first plastic member 12 operatively connected to a second metal member 11. The plastic member 12 is constructed from any suitable plastic material such as mylar, or any other plastic which is well known in the art for matrix bands. Similarly, the metal member 11 is constructed from a suitable metal such as stainless steel, as is well known in the art. Further, while the band 10 is shown as having a slightly curved profile, it is understood that other suitable shapes may be utilized. The plastic member 12 is generally elongate and has a first end 12a and a second end 12b. Further, the metal member 11 is generally elongate and has a first end 11a and a second end 11b. The second end 12b is operatively connected to the first end 11a by suitable means. One such method is a laminating procedure such as where the metal is microetched and placed against the plastic member 12 and then heat sealed to operatively connect the two members. Alternately, the plastic and metal members 11 and 12 may be simply glued together by use of a suitable epoxy cement. As shown in FIG. 2, there is an overlap between the members 11 and 12 and it is in the overlap area where the members 11 and 12 are connected.

A second embodiment of the invention is shown in FIGS. 3 and 4. There is generally disclosed a modified matrix band 20 having a first plastic member 23 and two metal members 21 and 22. The plastic member 23 has a first end 23a and a second end 23b. The first metal member has a first end 21a and a second end 21b. Similarly, the second metal member 22 has a first end 22a and a second end 22b. The first end 23a of the plastic member 23a is operatively connected to the second end 22a of the metal member 22 and the second end 23b of the plastic member 23 is operatively connected to the first end 21a of the metal member 21. The members are operatively connected in a manner similar to that described with respect to the first embodiment shown in FIGS. 1 and 2 and are constructed of similar materials as the first embodiment. Also, FIG. 4 shows that the plastic member 23 extends only partially over the metal members 21 and 22. Depending upon the techniques used, the amount of overlap could either be increased or decreased. Similar to the first embodiment, the overall shape of the matrix band 20 may be modified. Still further, the thickness and material of the bands 10 and 20 are similar to those well known in the art for just all plastic or for all metal bands.

In operation, the use of the first matrix band 10 is shown in FIG. 5. A first tooth 41 has a prepared cavity area 41a. Adjacent the first tooth 41 is a second tooth 42 and a third tooth 40. Between the first tooth 41 and second tooth 42 is a closed contact area, designated as 41b. There is an open contact area between the third tooth 40 and first tooth 41. The band 10 is used with a Tofflemire retainer 30, which is well known in the art. In addition, operation of such a retainer is also well known in the art and is described in U.S. Pat. No. 2,594,367, which is hereby incorporated by reference. After preparing the cavity to be filled, the matrix band 10 is inserted on the retainer 30 and the band 10 is positioned so that the metal member 11 is inserted between the first tooth 41 and the second tooth 42 at the contact point 41b and the plastic member 12 is positioned in front of the prepared cavity area 41a. A light cured composite resin is then applied to the prepared cavity area 41a. Then, the composite resin is cured with a light. Any suitable light cured composite resin and curing light may be used, both of which are well known in the art.

In operation, the use of the second matrix band 20 is shown in FIG. 6. A first tooth 51 has a prepared cavity area 51a. Adjacent the first tooth 51 is a second tooth 52 and a third tooth 50. Between the first tooth 51 and second tooth 52 is a closed contact area, designated as 51b. There is an closed contact area between the third tooth 50 and first tooth 51 designated at 51c. The band 20 is used with a Tofflemire retainer 30, which is well known in the art. After preparing the cavity to be filled, the matrix band 20 is inserted on the retainer 30 and is positioned so that the metal member 21 is inserted between the first tooth 51 and the second tooth 52 at the contact point 51b. The metal member 22 is inserted between the first tooth 51 and the third tooth 50 at the contact point 51c and the plastic member 22 is positioned in front of the prepared cavity area 51a. A light cured composite resin is then applied to the prepared cavity area 51a. Then, the composite resin is cured with a light. Any suitable light cured composite resin and curing light may be used, both of which are well known in the art. In FIGS. 5 and 6, the contact points 41b, 51b and 51c may, at times, appear to be spaced apart and not in close contact. However, they are shown this way only so that the bands 10 and 20 may be shown between the teeth. Even though illustrated this way, they are contact points.

The matrix bands 10 and 20 make placement of posterior composites easier and with this easier use will result in greater acceptance and use of this material by dentists. The plastic portions of each band 10 and 20 may be easily placed where the contact has been drilled away for the cavity preparation and the metal portions of the bands 10 and 12 easily slip through the contact area with no wedging. This eliminates patient discomfort from wedging and the resulting blood contamination of the field of operation. It also saves the dentist valuable chair time and the frustration of matrix placement. The bands 10 and 20 allow the dentist to place light cured posterior composition resins more easily by giving them a more user friendly matrix band. The prior art bands are either not usable because of the all metal design, which can not be used with light cured fillings, or do not address the problems of placing the all plastic matrix between the contact points of the teeth.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having specific configurations and shapes as presented herein. All alternative modifications and variations of the present invention which follow in the spirit and broad scope of the appended claims are included.

I claim:

1. A modified dental matrix band for engaging around a first tooth having a prepared cavity area and the first tooth having a contact point with a second tooth, comprising:
   (a) a first plastic member;
   (b) a second metal member sized and configured for insertion between the first and second teeth at the contact point; and
   (c) said first member operatively connected to said second member, thereby forming a modified matrix band having the metal member for insertion between the first and second teeth at the contact point and the plastic member positioned adjacent the prepared cavity area, wherein a fiber optic light may pass through the plastic member to the prepared cavity area.

2. The band of claim 1, wherein said first plastic member is elongate and has first and second ends and said second metal member is elongate and has first and second ends, said second end of said plastic member adjacent said first end of said metal member.

3. A modified dental matrix band for engaging around a first tooth having a prepared cavity area and the first tooth having a first contact point with a second tooth and a second contact point with a third tooth, comprising:
   (a) a first plastic member having first and second ends;
   (b) a second metal member having first and second ends;
   (c) a third metal member having first and second ends; and
   (d) said first end of said first member operatively connected to said first end of said second member and said second end of said first member operatively connected to said first end of said third member, thereby forming a modified matrix band having the first metal member for insertion between said first and second teeth at the first contact point and the plastic member positioned adjacent the prepared cavity area and the second metal member for insertion between said first and third teeth at the second contact point, wherein a fiber optic light may pass through the plastic member to the prepared cavity area.

4. A method of filling a cavity in a first tooth and the first tooth having a contact point with a second tooth, comprising:
   (a) preparing the cavity to be filled;
   (b) positioning a matrix band having a metal member and a plastic member around the first tooth so that the metal member is inserted between the first and second tooth at the contact point and positioning the plastic portion proximate the cavity;
   (c) applying a light cured composite resin to the cavity; and
   (d) curing the composite resin with a light.

5. A method of filling a cavity in a first tooth and the first tooth having a first contact point with a second tooth and a second contact point with a third tooth, comprising:
   (a) preparing the cavity to be filled;
   (b) positioning a matrix band, having a plastic member positioned between a first metal member and a second metal member, around the first tooth so that the first metal member is inserted between the first and second teeth at the first contact point and the second metal member is inserted between the first and third teeth at the second contact point and positioning the plastic portion proximate the cavity;
   (c) applying a light cured composite resin to the cavity; and
   (d) curing the composite resin with a light.

6. A modified dental matrix band for engaging around a first tooth having a prepared cavity area and the first tooth having a contact point with a second tooth, comprising:
   (a) a first plastic member;
   (b) a second metal member, said first member and said second member are approximately equal in length; and
   (c) said first member operatively connected to said second member, thereby forming a modified matrix band having the metal member for insertion between the first and second teeth at the contact point and the plastic member positioned adjacent the prepared cavity area, wherein a fiber optic light may pass through the plastic member to the prepared cavity area.

* * * * *